(12) United States Patent
Uozumi et al.

(10) Patent No.: US 9,340,764 B2
(45) Date of Patent: May 17, 2016

(54) TRANSFER DEVICE FOR CULTURE VESSEL, CULTURE DEVICE AND HOLDER FOR CULTURE VESSEL

(75) Inventors: Takayuki Uozumi, Tokyo (JP); Yasujiro Kiyota, Tokyo (JP); Nobuhiko Maiya, Kanagawa (JP); Hirofumi Shiono, Kanagawa (JP)

(73) Assignee: NIKON CORPORATION, Tokyo (JP)

( * ) Notice: Subject to any disclaimer, the term of this patent is extended or adjusted under 35 U.S.C. 154(b) by 266 days.

(21) Appl. No.: 11/921,077

(22) PCT Filed: Jun. 27, 2006

(86) PCT No.: PCT/JP2006/312819
§ 371 (c)(1),
(2), (4) Date: Nov. 27, 2007

(87) PCT Pub. No.: WO2007/001002
PCT Pub. Date: Jan. 4, 2007

(65) Prior Publication Data
US 2010/0047902 A1    Feb. 25, 2010

(30) Foreign Application Priority Data

Jun. 29, 2005  (JP) ................................. 2005-189337
Jun. 29, 2005  (JP) ................................. 2005-189338
Oct. 4, 2005   (JP) ................................. 2005-290897

(51) Int. Cl.
*C12M 1/00*   (2006.01)
*C12M 3/00*   (2006.01)

(52) U.S. Cl.
CPC ............... *C12M 23/50* (2013.01); *C12M 23/48* (2013.01)

(58) Field of Classification Search
CPC .............................. C12M 23/50; C12M 23/48
USPC ............................................ 435/286.2–286.4
See application file for complete search history.

(56) References Cited

U.S. PATENT DOCUMENTS

| | | | |
|---|---|---|---|
| 6,673,595 B2* | 1/2004 | Barbera-Guillem | 435/286.2 |
| 2003/0040104 A1* | 2/2003 | Barbera-Guillem | 435/286.2 |
| 2004/0152188 A1* | 8/2004 | Yamamoto et al. | 435/287.3 |
| 2005/0260742 A1 | 11/2005 | Watanabe | |
| 2006/0115892 A1 | 6/2006 | Yamamoto et al. | |

FOREIGN PATENT DOCUMENTS

| | | |
|---|---|---|
| JP | U-61-098500 | 6/1986 |
| JP | A-61-152273 | 7/1986 |
| JP | A-2003-235544 | 8/2003 |
| JP | A-2004-180675 | 7/2004 |
| JP | A-2004-344126 | 12/2004 |
| JP | A-2005-333823 | 12/2005 |
| JP | A-2006-101781 | 4/2006 |

* cited by examiner

*Primary Examiner* — Jonathan Hurst
(74) *Attorney, Agent, or Firm* — Oliff PLC

(57) ABSTRACT

A transfer device for a culture vessel for transferring a culture vessel for culturing a cell, a culture device including the transfer device for a culture vessel, and a holder for a culture vessel for holding a culture vessel, in which the transfer device for a culture vessel includes a transferring unit transferring a culture vessel for culturing a cell, an inputting unit inputting a kind of the culture vessel, a speed setting unit setting a transfer speed of the culture vessel based on a kind of the culture vessel inputted to the inputting unit, and a controlling unit controlling a transfer speed of the transferring unit to be the transfer speed set by the speed setting unit.

6 Claims, 15 Drawing Sheets

Fig. 2
(a)
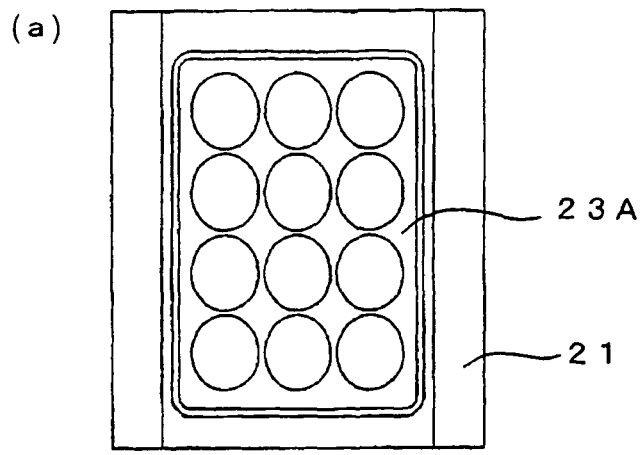
(b)
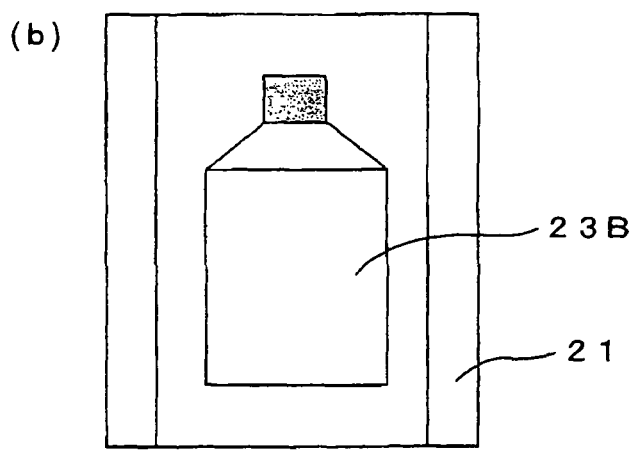
(c)
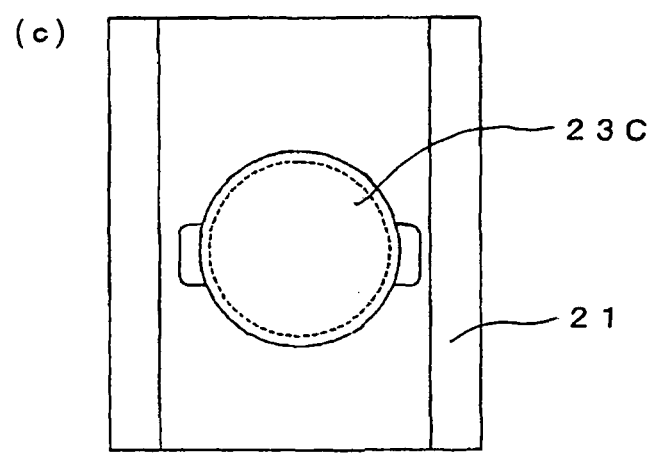

TRANSFER DEVICE FOR CULTURE VESSEL, CULTURE DEVICE AND HOLDER FOR CULTURE VESSEL

CROSS-REFERENCE TO RELATED APPLICATION

This application is a U.S. National Stage application claiming the benefit of prior filed International Application Number PCT/JP2006/312819, filed Jun. 27, 2006, in which the International Application claims priorities from Japanese Application Numbers 2005-189337 (filed on Jun. 29, 2005), 2005-189338 (filed on Jun. 29, 2005), and 2005-290897 (filed on Oct. 4, 2005) the entire contents of which are incorporated herein by reference.

TECHNICAL FIELD

The present invention relates to a transfer device for a culture vessel for transferring a culture vessel for culturing cells, a culture device including the transfer device for the culture vessel, and a holder for the culture vessel holding the culture vessel.

BACKGROUND ART

In a background art, there is a culture device for arranging a stacker including a number of shelves at inside of a chamber maintained in a predetermined atmosphere and culturing cells at inside of a culture vessel contained at each of the shelves. Further, according to the culture device, transferring in and transferring out of the culture vessel to and from each of the shelves are carried out by a transfer device arranged at inside of the chamber. That is, for example, when the culture vessel is transferred in to the shelf, the culture vessel placed at a transfer inlet/outlet formed to the chamber is transferred to a predetermined shelf by the transfer device. Further, when the culture vessel is transferred out, the culture vessel at the predetermined shelf is transferred to the transfer inlet/outlet by the transfer device.
Patent Document 1: Japanese Unexamined Patent Application Publication No. 2004-180675
Patent Document 2: Japanese Unexamined Patent Application Publication No. 2004-344126

DISCLOSURE

Problems to be Solved

However, it is an object of the transfer device of the background art to convey a well plate constituting one of the culture vessel swiftly to the transfer inlet/outlet, for example, when the culture vessel other than the well plate is transferred, there poses a problem that an enormous burden is operated to cells by shaking a culture solution at inside of the culture vessel and there is a concern that cells at inside of the culture vessel are exfoliated from a bottom face and become extinct. Further, the concern that the cells at inside of the culture vessel become extinct is significantly changed also by a kind or a state of the cells cultured in the culture vessel. Further, there poses a problem that there is a concern of leaking the culture solution by shaking the culture solution at inside of the culture vessel to contaminate inside of the culture device.

The invention has been carried out in order to resolve the background art problem and it is an object thereof to provide a transfer device for a culture vessel and a culture device capable of transferring a culture vessel for culturing cells at an optimum speed.

Further, it is an object thereof to provide a holder for a culture vessel capable of constituting a height of the culture vessel up to an inner bottom face thereof by a predetermined height regardless of a kind and a size of the culture vessel.

Further, it is an object thereof to provide a holder for a culture vessel capable of easily and firmly positioning a holder at a predetermined position of an observation stage.

Means for Solving the Problems

A transfer device for a culture vessel of a first aspect of the invention is characterized in including a transferring unit for transferring a culture vessel for culturing a cell, an inputting unit for inputting a kind of the culture vessel, a speed setting unit for setting a transfer speed of the culture vessel based on a kind of the culture vessel inputted by the inputting unit, and a controlling unit for controlling a transfer speed of the transferring unit to be the transfer speed set by the speed setting unit.

The transfer device for a culture vessel of a second aspect of the invention is characterized in that a kind of the culture vessel is a well plate, a flask or a dish in the transfer device for the culture vessel of the first aspect of the invention.

A transfer device for a culture vessel of a third aspect of the invention is characterized in including a transferring unit for transferring a culture vessel for cultivating a cell, an inputting unit for inputting information of the cell cultured at inside of the culture vessel, a speed setting unit for setting a transfer speed of the culture vessel based on the information of the cell inputted by the inputting unit, and a controlling unit for controlling a transfer speed of the transferring unit to be the transfer speed set by the speed setting unit.

The transfer device for a culture vessel of a fourth aspect of the invention is characterized in that information of the cell is a kind of the cell or a state of the cell in the transfer device for a culture vessel of the third aspect of the invention.

The transfer device for a culture vessel of a fifth aspect of the invention is characterized in that the speed setting unit sets the transfer speed based on a past historical data of the culture vessel in the transfer device for a culture vessel of the first aspect of the invention.

The transfer device for a culture vessel of a sixth aspect of the invention is characterized in that the speed setting unit sets the transfer speed based on a past historical data of the culture vessel in the transfer device for a culture vessel of the third aspect of the invention.

A culture device of a seventh aspect of the invention is characterized in including the transfer device for a culture vessel of the first aspect of the invention.

A culture device of an eighth aspect of the invention is characterized in including the transfer device for a culture vessel of the third aspect of the invention.

A holder for a culture vessel of a ninth aspect of the invention is characterized in a holder for a culture vessel mounted with a culture vessel contained at inside of a culture receptacle and conveyed to inside of the culture receptacle along with the culture vessel, the holder for a culture vessel including a holder main body formed with a mounting face where a plurality of the culture vessels having different outer shapes are mounted on, and a culture vessel holding unit holding a varieties of the culture vessels having the different outer shapes, the culture vessel holding unit being provided at the holder main body and corresponds to the culture vessels.

The holder for a culture vessel of a tenth aspect of the invention is characterized in that the culture vessel holding unit includes a three point support mechanism for determining a position of the culture vessel mounted on the holder main body in the holder for the culture vessel of the ninth aspect of the invention.

The holder for a culture vessel of an eleventh aspect of the invention is characterized in that the culture vessel holding unit includes a template for determining a position of the culture vessel mounted on the holder main body in the holder for a culture vessel of the ninth aspect of the invention.

The holder for a culture vessel of a twelfth aspect of the invention is characterized in that the template is formed with a hole for positioning the culture vessel in the holder for a culture vessel of the eleventh aspect of the invention.

A holder for a culture vessel of a thirteenth aspect of the invention is characterized in a holder for a culture vessel mounted with a culture vessel contained at inside of a culture receptacle and conveyed to inside of the culture receptacle along with the culture vessel, the holder for a culture vessel including a holder main body formed with a mounting face where the culture vessel is mounted on, and a height adjusting member for adjusting a height of and horizontally maintaining an inner bottom face of the culture vessel and being provided at a face on a back side of a mounting face of the holder main body.

The holder for a culture vessel of a fourteen aspect of the invention is characterized in that the height adjusting member is formed integrally with the holder main body, wherein a plurality of the holders for the culture vessels include the height adjusting members which differ from each other in the holder for a culture vessel of the thirteenth aspect of the invention.

The holder for a culture vessel of a fifteenth aspect of the invention is characterized in that the height adjusting member is attachably and detachably provided to the holder main body in the holder for a culture vessel of the thirteenth aspect of the invention.

The holder for a culture vessel of a sixteenth aspect of the invention is characterized in that the mounting face of the holder main body of each of a plurality of the holders for the culture vessels includes a holding unit for holding respective different kinds of the culture vessels, wherein the height adjusting member of each of the plurality of holders for the culture vessels is provided with height by which inner bottom faces of the culture vessel is adjusted to the same height, the culture vessel being mounted on said respective holder main body, in the holder for a culture vessel of the thirteenth aspect of the invention.

The holder for a culture vessel of a seventeenth aspect of the invention is characterized in that each of the holder main bodies of a plurality of the holders for the culture vessels having different outer shapes are formed into the same shape of the outer shape, and each of the holder main bodies are formed with the same positioning unit for positioning the holder main bodies on the observation stage in the holder for a culture vessel of the ninth aspect of the invention.

The holder for a culture vessel of an eighteenth aspect of the invention is characterized in that the positioning unit includes a concave portion formed at the holder main body and fitted to a positioning pin of the observation stage in the holder for a culture vessel of the seventeenth aspect of the invention.

The holder for a culture vessel of a nineteenth aspect of the invention is characterized in that the holder main body is mounted with a transparent wall thickness adjusting sheet having a wall thickness which differs in accordance with a wall thickness of a bottom face of the culture vessel mounted on the holder main body and the culture vessel is mounted on the wall thickness adjusting sheet in the holder for a culture vessel of the seventeenth aspect of the invention.

The holder for a culture vessel of a twentieth aspect of the invention is characterized in that the wall thickness adjusting sheet includes the same material as that of the culture vessel mounted on the holder main body in the holder for a culture vessel of the nineteenth aspect of the invention.

The holder for a culture vessel of a twenty-first aspect of the invention is characterized in that the holder main body includes a transparent resin in the holder for a culture vessel of the ninth aspect of the ninth aspect of the invention.

BRIEF DESCRIPTION OF THE DRAWINGS

FIG. 2 illustrates explanatory views showing a kind of a culture vessel contained in the culture device of FIG. 1;

FIG. 3 is an explanatory diagram showing a control operation when the culture vessel of the culture device of FIG. 1 is transferred in;

DETAILED DESCRIPTION OF THE EMBODIMENTS

Embodiments of the invention will be explained in details in reference to the drawings as follows.

First Embodiment

Figure 1:
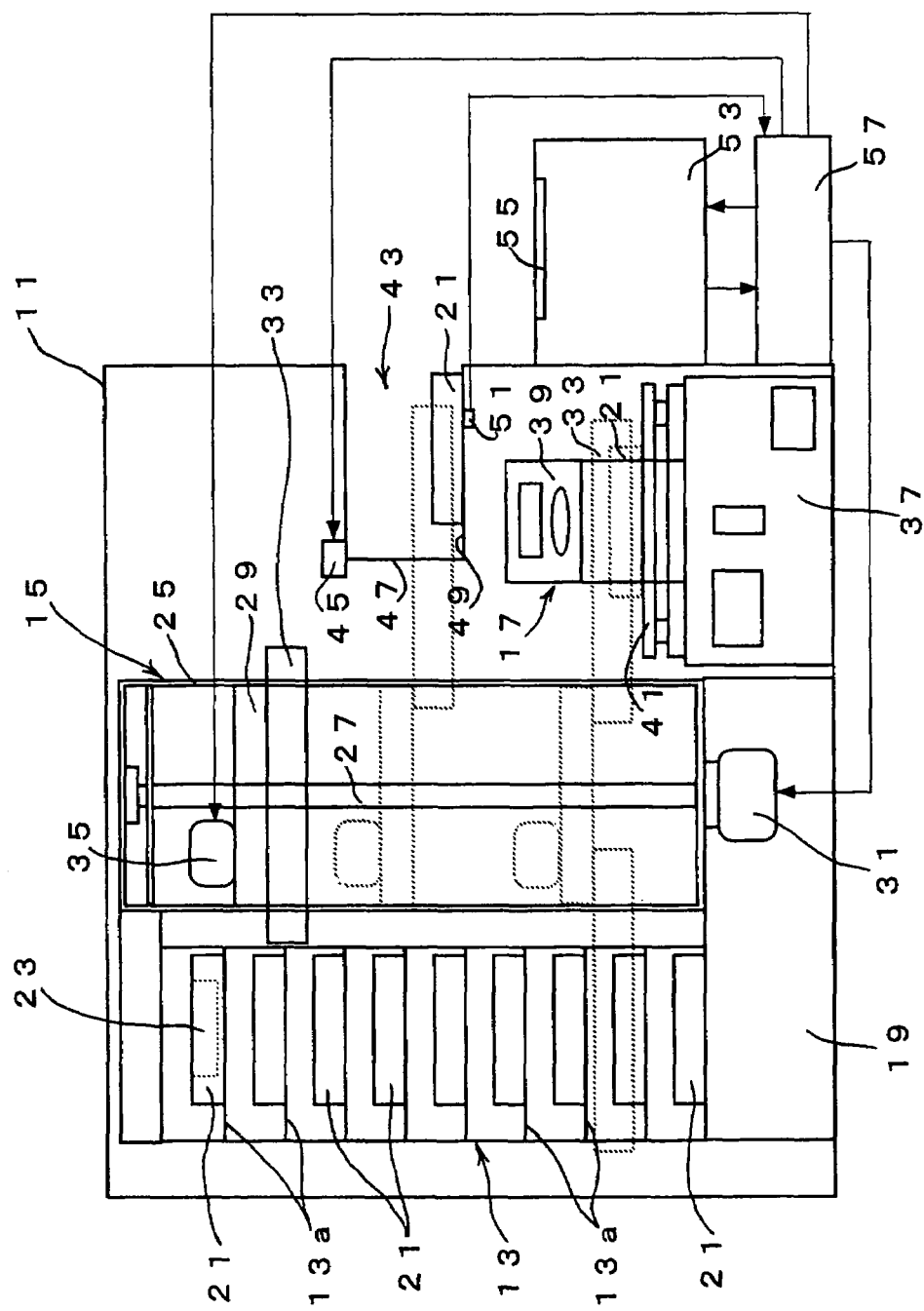
FIG. 1 is an explanatory view showing an embodiment of a culture device of the invention.

FIG. 1 shows an embodiment of a culture device of the invention.

The culture device includes a chamber 11 maintained in an atmosphere of a constant temperature and a constant humidity.

Inside of the chamber 11 is arranged with a stacker 13, a transfer device 15 and an observation device 17.

The stacker 13 is arranged above a base 19 and partitioned in an up and down direction by shelves 13a. Holders 21 are mounted at upper faces of the shelves 13a. At culture vessels 23 for culturing cells are held by the respective holders 21. According to the embodiment, as shown by FIGS. 2(a), (b), (c), the culture vessels 23 are constituted by 3 kinds of a well plate 23A, a flask 23B, and a dish 23C. Further, the respective culture vessels 23 are held by the holders 21 having the same shape and size by way of hold members (not illustrated).

The transfer device 15 includes a frame 25 arranged above the base 19. A center of the frame 25 is arranged with a screw shaft 27 in an up and down direction. The screw shaft 27 is screwed with a moving member 29 made to be movable in the up and down direction when the screw shaft 27 is rotated by a first motor 31. A lower side of the moving member 29 is arranged with a transfer arm 33 moved in the up and down direction along with the moving member 29. The transfer arm 33 is made to be movable in a horizontal direction by a drive mechanism (not illustrated) by a second motor 35.

The observation device 17 includes a microscope 39 arranged above a base 37. The microscope 39 is constituted by a simple type microscope having a comparatively low magnification. A sample base 41 for mounting the holder 21 transferred by the transfer arm 33 is arranged above the base 37. The sample base 41 is made to be movable in a horizontal direction (X and Y directions). By mounting the culture vessel 23 on the sample base 41, along with the holder 21, cells at inside of the culture vessel 23 are observed.

A transfer inlet/outlet 43 is formed at a position of a side face of the chamber 11 on an upper side of the microscope 39. A depth side of the transfer inlet/outlet 43 is arranged with a door 47 opened and closed by a third motor 45. An inner side of the transfer inlet/outlet 43 is arranged with a mounting portion 49 for mounting the holder 21. The mounting portion 49 is arranged with a sensor 51 for detecting presence/absence of the holder 21. The sensor 51 outputs a detecting signal when the holder 21 is mounted on the mounting portion 49.

An outer side of the side face of the chamber 11 is provided with an information input portion 53 for inputting a kind of the culture vessel 23 transferred in and from the transfer inlet/outlet 43 as well as a kind, a state or the like of cells cultured by the culture vessel 23. The information input portion 53 includes a liquid crystal display portion 55 and a touch sensor (not illustrated). Further, a lower side of the information input portion 53 is provided with a control portion 57 for controlling a transfer speed of the transfer arm 33. The control portion 57 controls the transfer speed of the transfer arm 33 by controlling revolution numbers of the first and the second motors 31, 35. Further, the door 47 is opened and closed by driving the third motor 45.

Figure 3:
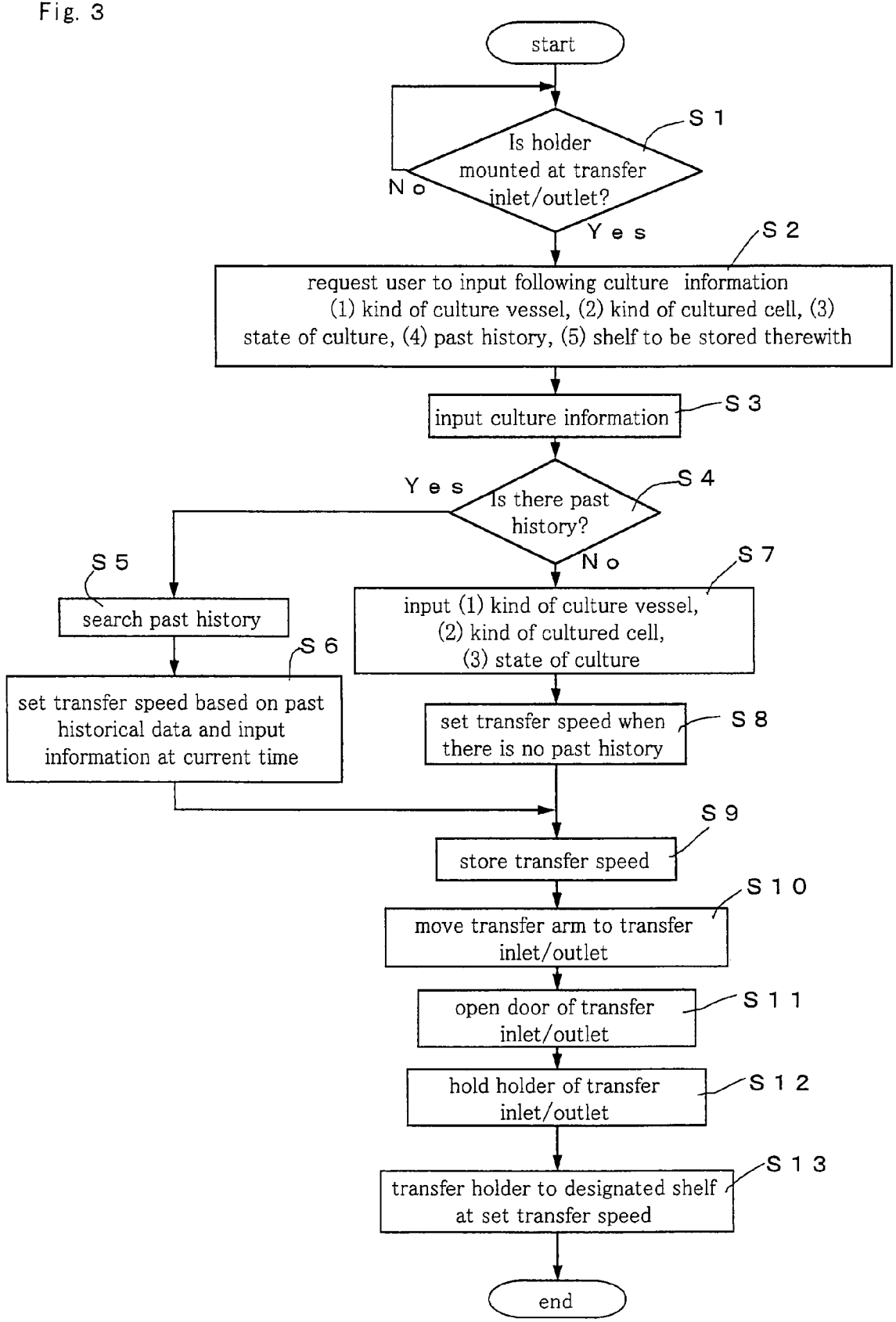

FIG. 3 is a flowchart for explaining an operation of the control portion 57 when the culture vessel 23 is transferred in at the culture device of the embodiment.

First, at step S1, it is determined whether the holder 21 is mounted on the mounting portion 49 of the transfer inlet/outlet 43. The determination is carried out by presence/absence of the detecting signal of the sensor 51, when the detecting signal is outputted from the sensor 51, it is determined that the holder 21 is mounted on the mounting portion 49.

Next, at step S2, a user is requested to input culture information. The request of the input is carried out by displaying input items at the liquid crystal display portion 55 of the information input portion 53. According to the embodiment, (1) a kind of a culture vessel 23, (2) a kind of cultured cells, (3) a state of culture, (4) presence/absence of a past history, (5) the shelf 13a to be stored therewith are displayed. The user carries out a predetermined input by touching the touch sensor (not illustrated) of the liquid crystal display portion 55 in correspondence with the display.

Here, (1) the input of the kind of the culture vessel 23 refers to input to which of the well plate 23A, the flask 23B, the dish 23C the culture vessel 23 corresponds and the input of the size of the culture vessel 23.

(2) The input of the kind of the cultured cells refers to the input of the kind of cells of Hela cells or the like.

(3) The input of the state of the culture refers to the input of the state of the culture immediately after passage, immediately after an experimental operation or the like.

(4) The input of the presence/absence of the past history refers to the input stating that the culture vessel 23 has been subjected to culture at inside of the chamber 11 in the past. According to the embodiment, the respective culture vessels 23 are attached with control numbers and the control numbers are inputted.

(5) The input of the shelf 13a to be stored therewith refers to designation of the shelf 13a to be stored therewith.

Next, at step S3, the culture information inputted at step S2 is inputted.

Next, at step S4, it is determined whether there is past history.

When there is the history, at step S5, the past history is searched from the inputted control number. According to the embodiment, the control portion 57 is stored with historical data of the culture vessel 23 in correspondence with the control number, that is, (1) the kind of the culture vessel 23, (2) the kind of the cultured cells, (3) the state of the culture mentioned above.

Next, at step S6, an optimum transfer speed of the transfer arm 33 is set based on the historical data and the information inputted at current time. For example, an elapsed time period after starting the culture and a grow situation are calculated from the historical data. Further, when, for example, the experimental operation is not carried out in the information inputted at current time, the transfer speed is set based on the historical data.

On the other hand, when there is not the past history, at step S7, (1) the kind of the culture vessel 23, (2) the kind of the cultured cells, (3) the state of the culture are inputted. Further, at step S8, the optimum transfer speed of the transfer arm 33 is set based on the input information.

The set optimum speed T1 is represented, for example, by the following equations.

$$T0 = f(A0, A1) \quad (1)$$

$$T1 = f(T0, A2) \quad (2)$$

A0: maximum speed (mm/sec) by which the culture solution in the kind of the culture vessel 23 does not spill A1: influence factor by vibration stress in the kind of the cell A2: influence factor by the state of the cell before being introduced to the culture device Specifically, assume that for example, the culture vessel 23 is constituted by a dish of Φ35 mm and a maximum speed by which when the culture solution (culture medium) is inputted up to a limit of the dish, a liquid level thereof remains untouched to a lid of the dish by vibration of transfer is T0=20 mm/sec. At this occasion, for example, when the Hela cells at inside of the culture vessel 23 are cells which are hardly influenced by a stress by vibration, the influence of the factor A1 is made to be able to be disregarded and the maximum speed at inside of the culture device stays to be 20 mm/sec. Further, the optimum transfer speed is set so as not to exceed the maximum speed.

On the other hand, when passage operation has been carried out before being introduced to the culture device according to the input information from the user, the cells are brought into a state of being floated in the culture solution, and therefore, the influence of the stress in being transferred is intensified in comparison with that in the adhered state. By substituting a rate of the influence for the factor A2, the maximum speed T1 is reduced to, for example, about T1=16 mm/sec and the optimum transfer speed is set so as not to exceed the speed.

Next, at step S9, the optimum transfer speed calculated at step S6 or step S8 is stored.

Next, at step S10, the transfer arm 33 is moved at the maximum speed of the transfer device 15 up to a front side of the door 47 of the transfer inlet/outlet 43.

Next, at step S11, the door 47 of the transfer inlet/outlet 43 is opened.

Next, at step S12, the transfer arm 33 is moved to hold the holder 21 mounted on the mounting portion 49.

Next, at step S13, the transfer arm 33 is moved at the transfer speed set at step S6 or step S9 and is contained to the shelf 13a designated at step S2.

Figure 4:
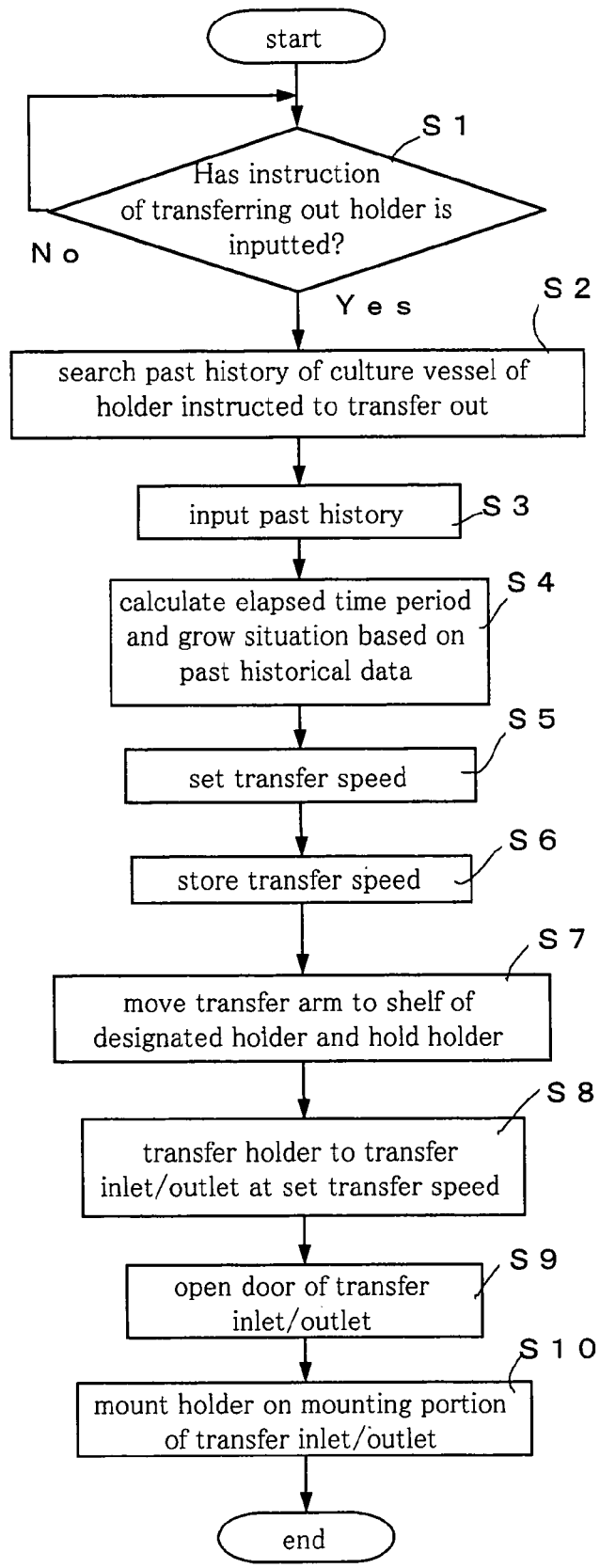
FIG. 4 is an explanatory diagram showing a control operation when the culture vessel of the culture device of FIG. 1 is transferred out.

FIG. 4 is a flowchart showing an operation of the control portion 57 when the culture vessel 23 is transferred out in the culture device of the embodiment.

First, at step S1, it is determined whether instruction of transferring out the holder 21 is inputted from the user. According to the embodiment, it is determined that the instruction of the transferring out the holder 21 is inputted by inputting the control number of the holder 21 to be transferred out to the information input portion 53 by the user.

Next, at step S2, the past history of the culture vessel 23 of the holder 21 instructed to be transferred out is searched from the inputted control number.

Next, at step S3, the past history is inputted.

Next, at step S4, the elapsed time period and the grow situation are calculated from the past historical data.

Next, at step S5, the optimum transfer speed of the transfer arm 33 is set based on the information.

For example, conceive a case in which the culture vessel 23 is stored at inside of the culture device and a constant time period t2 has elapsed. At this occasion, when normal culture is progressed, at inside of the culture vessel 23, cells sink to the bottom face of the culture vessel 23 to be brought into a state of being adhered to the bottom face.

A speed T2 after elapse of the constant time period is shown by the following equation.

$$T2 = f(T1, t2, A3) \quad (3)$$

T1: optimum speed (mm/sec) determined in transferring in the culture vessel 23 t2: elapsed time period from transfer in to the culture device

A3: grow situation factor of cell

For example, assume that the optimum speed in being transferred in is T1=16 mm/sec and assume that about 10 hours has elapsed from transfer in of the culture vessel 23 and it can be predicted that cells are adhering to the bottom face of the culture vessel 23 without a problem. At this occasion, cells adhere to the bottom face of the culture vessel 23 in accordance with the elapse of the elapsed time period t2, and therefore, it can be determined that an influence by the stress in transferring the cells is reduced. Therefore, by substituting, for example, the elapsed time period and the factor of the grow situation for t2 and A3, the optimum speed T2 after elapse of the constant time period is recovered to, for example, about T2=18 mm/sec. However, the optimum speed is not equal to or faster than the maximum speed T0=20 mm/sec.

Further, when normal culture is not brought about, cells do not adhere to the bottom face and stay to be floated on the culture solution, and therefore, by observing the situation by, for example, the observing device 17, the transfer speed can further precisely be set.

Next, at step S6, the set transfer speed is stored.

Next, at step S7, the transfer arm 33 is moved to the shelf 13a of the designated holder 21 at the maximum speed of the transfer device 15 and holds the holder 21.

Next, at step S8, the transfer arm 33 is moved to the front side of the door 47 of the transfer inlet/outlet 43 at the transfer speed set at step S5.

Next, at step S9, the door 47 of the transfer inlet/outlet 43 is opened.

Next, at step S10, the transfer arm 33 is moved to mount the holder 21 on the mounting portion 49.

According to the above-described culture device, the transfer speed of the culture vessel 23 is set based on the kind of the culture vessel 23, and therefore, it can be resolved that the culture solution is leaked by shaking the culture solution at inside of the culture vessel 23 to contaminate inside of the culture device. Further, there can be resolved the concern that enormous burden is operated on cells by shaking the culture solution at inside of the culture vessel 23 and the cells at inside of the culture vessel 23 are exfoliated from the bottom face to become extinct.

Further, since according to the above-described culture device, the transfer speed of the culture vessel 23 is set based on the information of the cells, there can be resolved the concern that enormous burden is operated on cells by shaking the culture solution at inside of the culture vessel 23 and the cells at inside of the culture vessel 23 are exfoliated from the bottom face to become extinct.

Second Embodiment

An embodiment of a holder for a culture vessel of the invention will be explained as follows.

Figure 5:
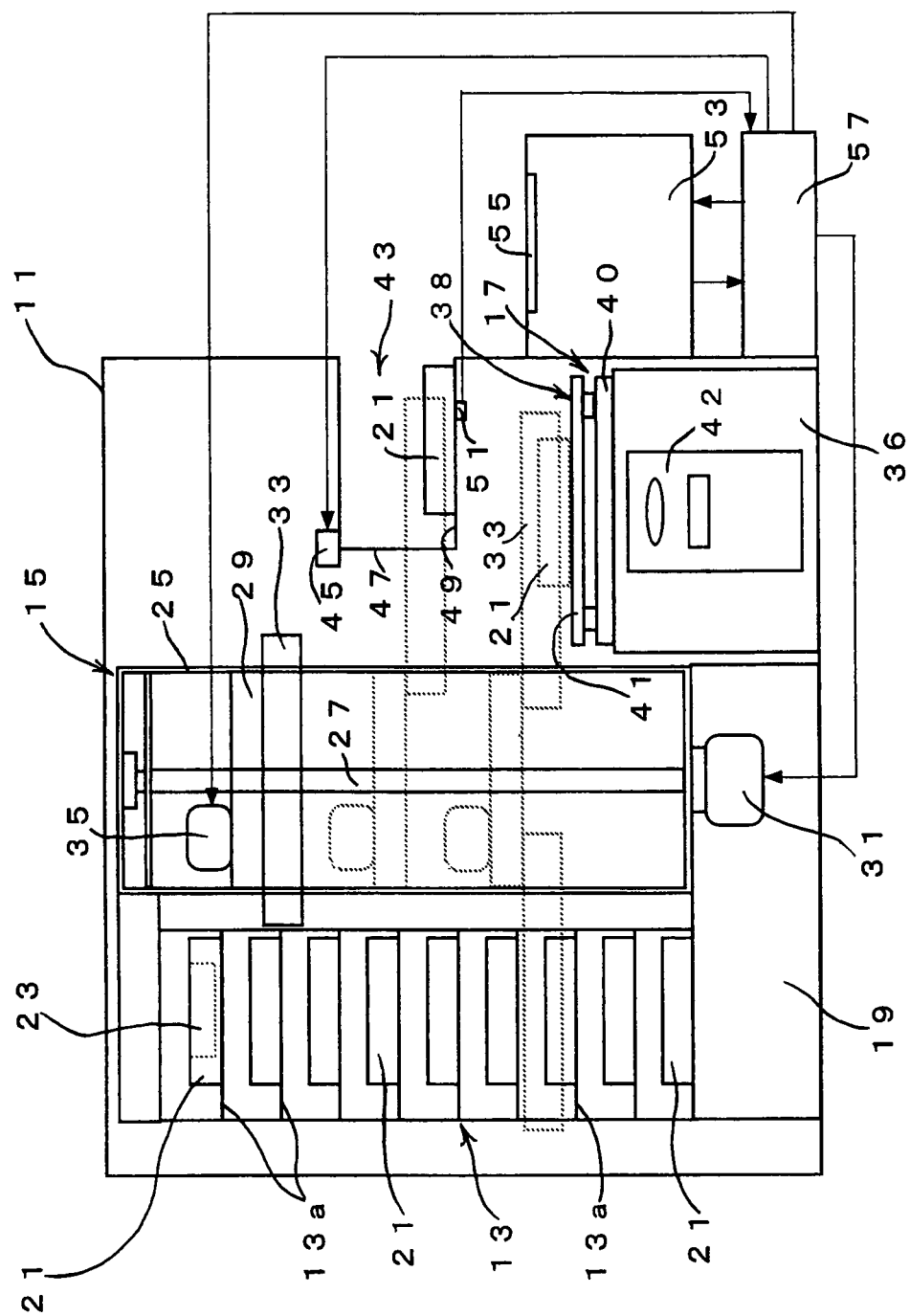
FIG. 5 is an explanatory view showing a culture device in which an embodiment of a holder for a culture vessel of the invention is used.

FIG. 5 shows a culture device in which an embodiment of a holder for a culture vessel of the invention is used. Further, according to the embodiment, members the same as those of the first embodiment are attached with the same notations and a detailed explanation thereof will be omitted.

The culture device includes the chamber 11 maintained at an atmosphere of a constant temperature and a constant humidity. Inside of the chamber 11 is attached with the stacker 13, the transfer device 15 and the observation device 17. The stacker 13 is arranged above the base 19 and is partitioned in the up and down direction by the shelves 13a. The holders 21 are mounted at the upper faces of the shelves 13a. The culture vessels 23 for culturing cells are held by the respective holders 21.

The transfer device 15 includes the frame 25 arranged above the base 19. The center of the frame 25 is arranged with the screw shaft 27 in the up and down direction. The screw shaft 27 is screwed with the moving member 29, which is made to be movable in the up and down direction when the screw shaft 27 is rotated by the first motor 31. The lower side of the moving member 29 is arranged with the transfer arm 33 moved in the up and down direction along with the moving member 29. The transfer arm 33 is made to be movable in the horizontal direction by the drive mechanism (not illustrated) operated by the second motor 35.

The observation device 17 includes an observing portion 36 and an observation stage 38. The observing portion 36 is arranged with a microscope 42. The microscope 42 is constituted by an inverted type microscope. The observation stage 38 for mounting the holder 21 transferred by the transfer arm 33 is arranged above the observing portion 36. The observation stage 38 includes a base member 40 and the sample base 41. Cells at inside of the culture vessel 23 are observed by mounting the culture vessel 23 on the sample base 41 along with the holder 21.

The transfer inlet/outlet 43 is formed at a position of the side face of the chamber 11e on an upper side of the microscope 42. The depth side of the transfer inlet/outlet 43 is arranged with the door 47 opened and closed by the third motor 45. An inner side of the transfer inlet/outlet 43 is arranged with the mounting portion 49 for mounting the holder 21. The mounting portion 49 is arranged with the sensor 51 for detecting presence/absence of the holder 21. The sensor 51 outputs the detecting signal when the holder 21 is mounted on the mounting portion 49.

An outer side of the side face of the side chamber 11 is provided with the information input portion 53 for inputting various information. The information input portion 53 includes the liquid crystal display portion 55 and the touch sensor (not illustrated).

The lower side of the information input portion 53 is provided with the control portion 57 for moving the transfer arm 33. The control portion 57 moves the transfer arm 33 by controlling the first and the second motors 31, 35. Further, the door 47 is opened and closed by driving the third motor 45.

Further, when the information input portion 53 is inputted with the control number of the holder 21 to be observed by the observation device 17, the transfer arm 33 is moved and the holder 21 in correspondence with the control number is transferred from the shelf 13a of the stacker 13 onto the sample 41 of the observation device 17.

FIGS. 6(a), (b), (c) show the culture vessel 23 held by the holder 21. According to the embodiment, as the culture vessel 23, three kinds of the culture vessels 23 of the well plate 23A, the flask 23B, the dish 23C are used. Further, wall thicknesses of the bottom portions of the well plate 23A, the flask 23B, the dish 23C are respectively designated by notations t1, t2, t3.

Figure 7:
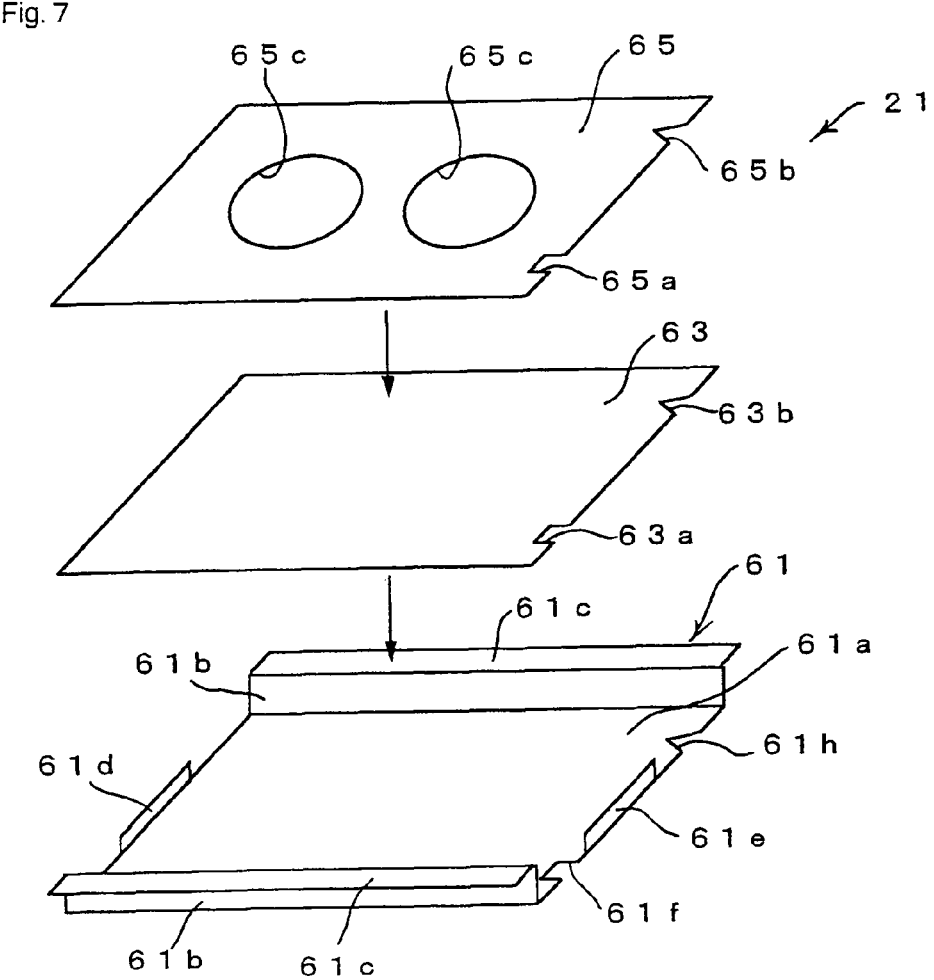
FIG. 7 is a disassembled perspective view showing details of the holder of FIG. 5.

FIG. 7 shows the holder 21 for holding the culture vessel 23. The holder 21 includes a holder main body 61. The holder main body 61 is formed by a white transparent resin. Both sides of a bottom portion 61a of the holder main body 61 are projected to an upper side to be formed with wall portions 61b. An upper end of the wall portion 61b is formed with a locking portion 61c for locking a transfer arm 133 (details of which will be described later) to be projected to an outer side. A projected portion 61d is formed on one side of the bottom portion 61a of the holder main body 61, and a reflecting portion 61e is formed on other side thereof. Further, rectangular and triangular concave portions 61f, 61h are formed at positions of the bottom portion 61a of the holder main body 61 constituting both sides of the reflecting portion 61e.

According to the embodiment, the bottom portion 61a of the holder main body 61 is arranged with a template 65 by way of a wall thickness adjusting sheet 63. The wall thickness adjusting sheet 63 and the template 65 are formed with concave portions 63a, 65a at positions in correspondence with the concave portion 61f formed at the bottom portion 61a of the holder main body 61. Further, concave portions 63b, 65b are formed at positions in correspondence with the concave portion 61h. The wall thickness adjusting sheet 63 is formed by a white transparent resin. The wall thickness adjusting sheet 63 is constituted by a wall thickness which differs in accordance with the wall thickness of the bottom face of the culture vessel 23 mounted on the holder main body 61 (for example, t1, t2, t3 of FIG. 6). The template 65 is formed by a resin, a metal or the like.

Figure 6:
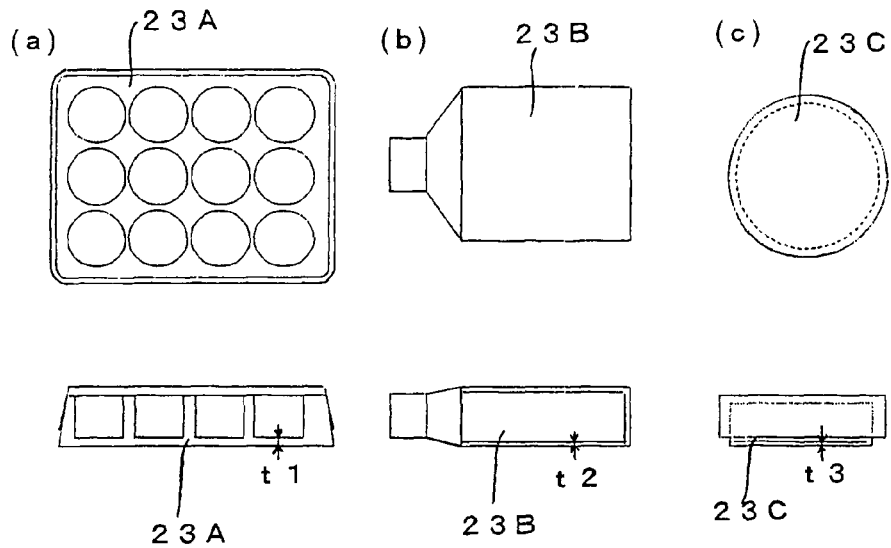
FIG. 6 illustrates explanatory views showing a kind of a culture vessel held by the holder of FIG. 5.

The template 65 is formed with a hole portion 65c for positioning the culture vessel 23. In FIG. 7, the hole portions 65c in a circular shape inserted with the bottom portions of the dishes 23C shown in FIG. 6 are formed at two portions. Further, a shape and a size of the hole portion 65c formed at the template 65 are determined in accordance with a kind and a size of the culture vessel 23 held by the holder 21. For example, when the well plate 23A or the flask 23B is used as the culture vessel 23, the hole portion is formed in correspondence with the shape and the size of the bottom portion of the well plate 23A or the flask 23B and positioning is carried out by inserting the bottom portion of the well plate 23A or the flask 23B to the hole portion.

Figure 8:
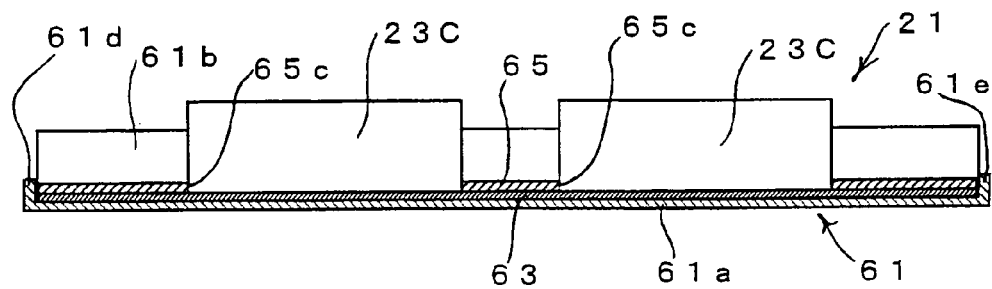
FIG. 8 is an explanatory view showing the holder of FIG. 7.

According to the holder 21, as shown by FIG. 8, the wall thickness adjusting sheet 63 is mounted at an upper face of the bottom portion 61a of the holder main body 61, and the template 65 is mounted on an upper face of the wall thickness adjusting sheet 63. Further, the bottom portion of the dish 23C is inserted into the hole portion 65c formed at the template 65. Thereby, the dish 23C is positioned at a predetermined position of the holder main body 61.

Figure 9:
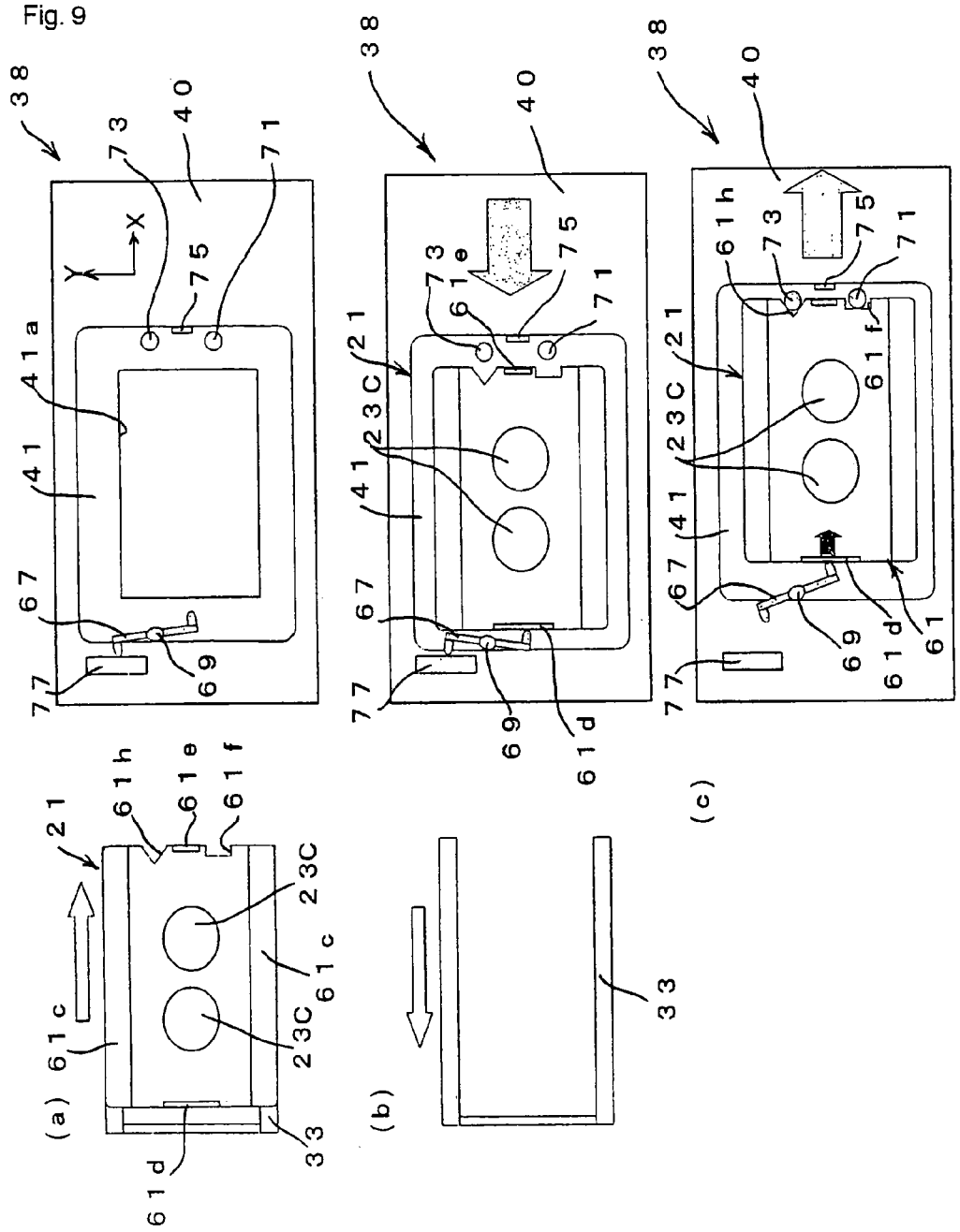
FIG. 9 is an explanatory view showing a structure of positioning the holder of FIG. 5 to an observation stage.

FIG. 9 shows details of the observation stage 38.

The sample base 41 is arranged on the base member 40 of the observation stage 38. The sample base 41 is made to be movable in the horizontal direction (X and Y directions) relative to the base member 40. The sample base 41 is arranged with an urging member 67. The urging member 67 is urged to be pivotable centering on a fulcrum 69 by a toggle spring (not illustrated). Positioning pins 71, 73 are arranged on a side opposed to the urging member 67 of the sample base 41. The sample base 41 is formed with a window portion 41a for observing from the lower side by the microscope 42. Further, an infrared ray sensor 75 is arranged between the positioning pins 71, 73 of the sample base 41.

The base member 40 is arranged with a pivot hampering member 77 for hampering pivoting of the urging member 67 arranged at the sample base 41. As shown by FIG. 9(a), when the sample base 41 is moved to a left side of the base member 40, the pivot hampering member 77 is brought into contact with the urging member 67 of the sample base 41 to hamper pivoting of the urging member 67.

According to the observation stage 38, as shown by FIG. 9(a), the holder 21 is transferred along with the culture vessel 23 on a lower side of the locking portion 61c of the holder main body 61 in a state of locking the transfer arm 33 of the transfer device 15. Under the state, the sample base 41 is disposed at a position on the left side of the base member 40. Thereby, the urging member 67 of the sample base 41 is brought into contact with the pivot hampering member 77 to thereby hamper the urging member 67 from being pivoted.

Further, under the state, as shown by FIG. 9(b), the holder 21 transferred by the transfer arm 33 is mounted to a predetermined position of the sample base 41. It is detected by the infrared ray sensor 75 whether the holder 21 is mounted on the sample base 41. That is, when the holder 21 is mounted on the predetermined position on the sample base 41, an infrared ray from the infrared ray sensor 75 is reflected by the reflecting portion 61e of the holder main body 61, and therefore, by detecting the reflected ray by the infrared ray sensor 75, presence/absence of the holder 21 can be detected.

Further, as shown by FIG. 9(c), when the sample base 41 is moved to a right side of the base member 40, the urging member 67 of the sample base 41 is separated from the pivot hampering member 77. Thereby, the urging member 67 is pivoted centering on the fulcrum 69 and the urging member 67 presses the projected portion 61d of the holder main body 61. By the pressing, the holder 21 is moved to the right side on the sample base 41, and the positioning pins 71, 73 are fitted to the concave portions 61f, 61 h of the holder main body 61. Thereby, the holder main body 61 is fixed between the urging member 67 and the positioning pins 71, 73 and is positioned at the predetermined position of the sample base 41.

Figure 10:
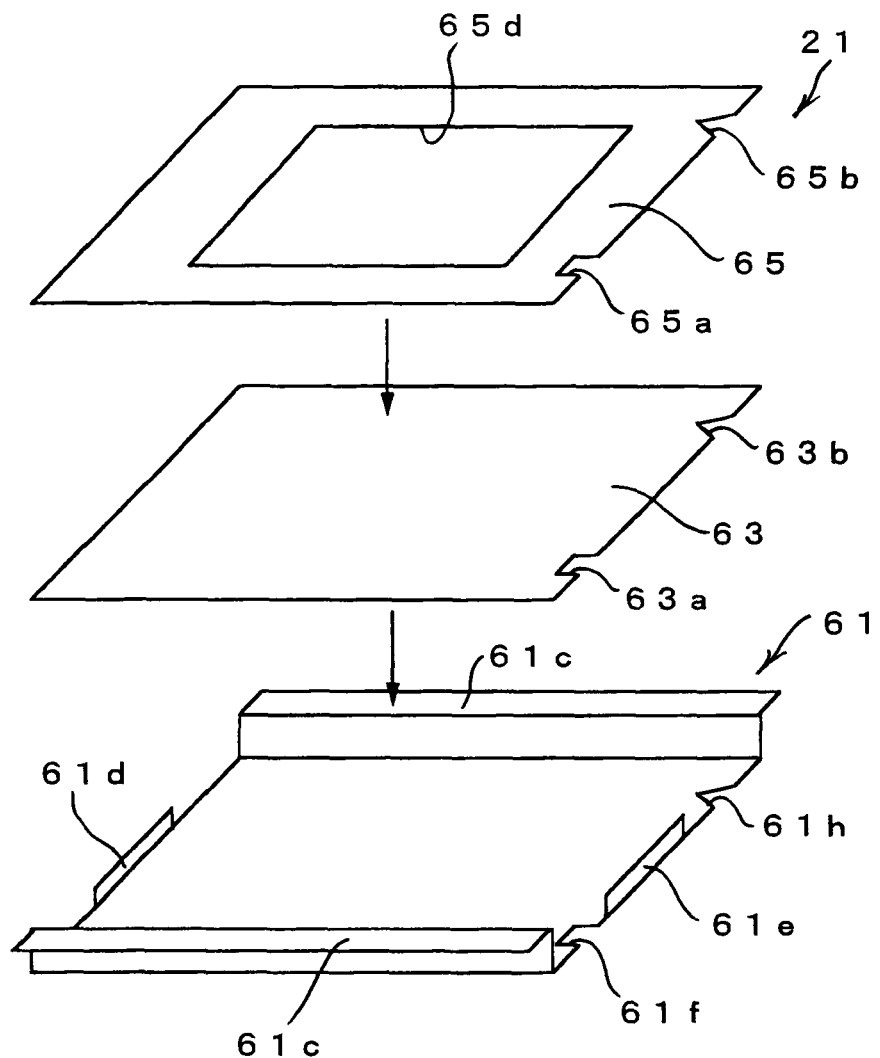
FIG. 10 is a disassembled perspective view showing details of other example of the holder of FIG. 5.

FIG. 10 shows the holder 21 used for transferring the flask 23B shown in FIG. 6. According to the holder 21, the template 65 shown in FIG. 9 is formed with a hole portion 65d in a rectangular shape which is a shape in correspondence with a shape of a bottom portion of the flask 23B. Further, the wall thickness of the wall thickness adjusting sheet 63 is changed in correspondence with a wall thickness of the bottom portion of the flask 23B. The holder main body 61 is the same as that of the holder 21 shown in FIG. 7.

Figure 11:
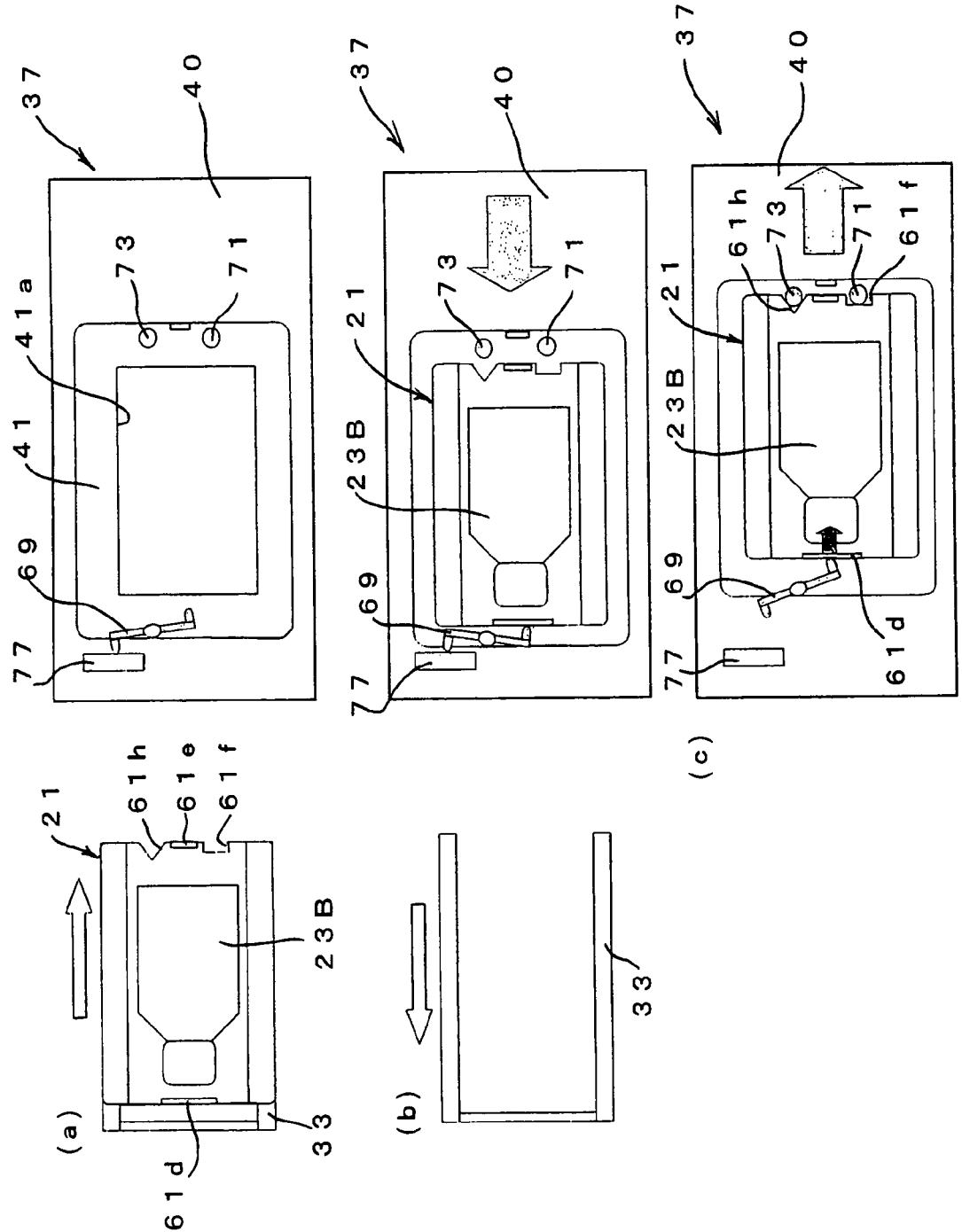
FIG. 11 illustrates explanatory views showing a structure of positioning the holder of FIG. 10 to an observation stage.

FIG. 11 shows a state of transferring the holder 21 to an observation stage 38 to be positioned on the sample base 41, and positioning onto to the sample base 41 is carried out similar to the holder 21 shown in FIG. 7.

According to the above-described holder for the culture vessel, the holder main body 61 transferred by being held by the transfer device 15 is formed with the concave portions 61f, 61h for positioning the holder main body 61 on the sample base 41 of the observation. stage 38, and therefore, the holder 21 can easily and firmly be positioned to a predetermined position of the sample base 41 of the observation stage 38.

Further, the holder main body 61 is arranged with the template 65 for determining the position of the culture vessel 23 mounted on the holder main body 61, and therefore, by changing a shape and a size of the hole portion 65c formed at the template 65, the culture vessel 23 can easily and firmly be transferred by the same transfer device 15 regardless of a kind and a size of the culture vessel 23.

Further, according to the above-described holder for the culture vessel, the holder main body 61 is mounted with the transparent wall thickness adjusting sheet 63 of a wall thickness which differs in accordance with the wall thickness of the bottom face of the culture vessel 23 mounted on the holder main body 61 and the culture vessel 23 is mounted on the wall thickness adjusting sheet 63, and therefore, regardless of the kind of the culture vessel 23, an optical path length from an object lens of the microscope 42 to a sample at inside of the culture vessel 23 can be made to stay the same and adjustment of a focal point of the microscope 42 can be facilitated.

That is, according to three kinds of the culture vessels 23 of the well plate 23A, the flask 23B, and the dish 23C, the wall thicknesses (for example, t1, t2, t3 of FIG. 6) of the bottom face of the culture vessels 23 respectively differ from each other, and therefore, when the wall thickness adjusting sheet 63 is not arranged, the optical lengths from the object lens of the microscope 42 to the sample in the culture vessels 23 respectively differ from each other and adjustment of the focal point of the microscope 42 becomes complicated. However, by thickening the wall thickness of the wall thickness adjusting sheet 63 when the wall thickness of the bottom face of the culture vessel 23 is thin and thinning the wall thickness of the wall thickness adjusting sheet 63 when the wall thickness of the bottom face of the culture vessel 23 is thick, regardless of the kind of the culture vessel 23, the optical length from the object lens of the microscope 42 to the sample in the culture vessel 23 can be made to stay the same and an adjustment of the focal point of the microscope 42 can be facilitated.

Further, by constituting a material of the wall thickness adjusting sheet 63 by a material the same as that of the culture vessel 23 mounted on the holder main body 61, an adjustment of the optical length is further facilitated.

Third Embodiment

Figure 12:
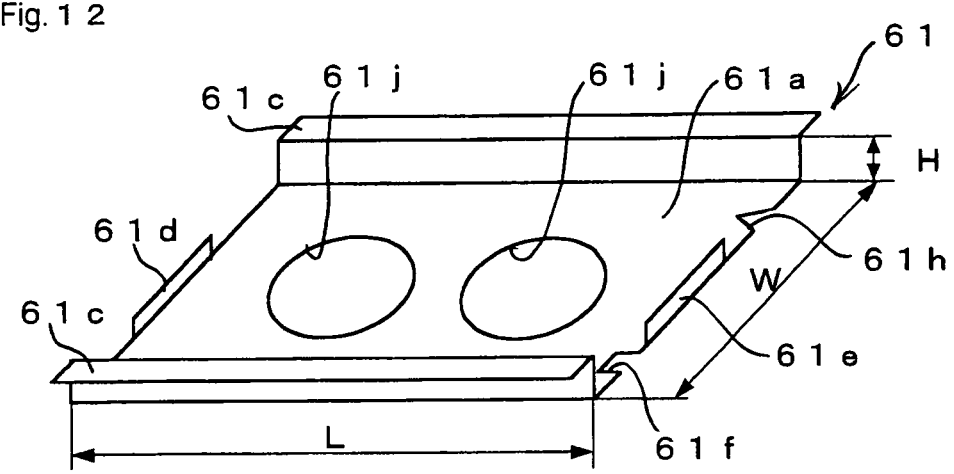
FIG. 12 is a disassembled perspective view showing other embodiment of a holder of the invention.
Figure 13:
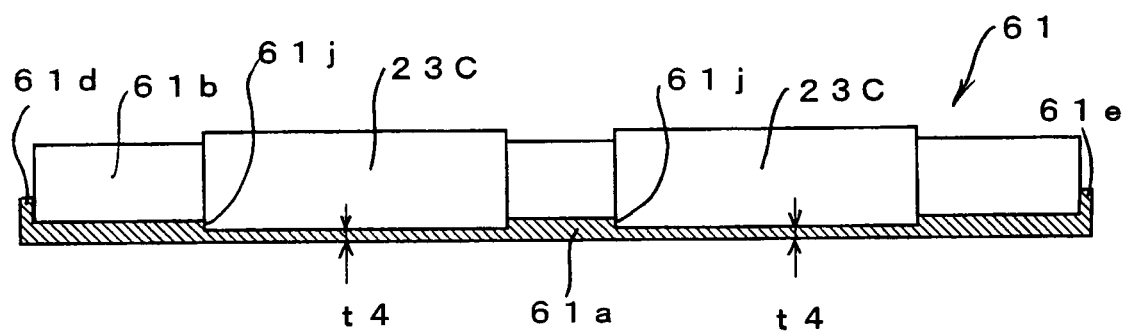
FIG. 13 is an explanatory view showing the holder of FIG. 12.

FIG. 12 and FIG. 13 show other embodiment of the holder for the culture vessel of the invention. Further, in the embodiment, portions the same as those of the second embodiment are attached with the same notations and a detailed explanation thereof will be omitted.

According to the embodiment, the holder main body 61 is formed by a white transparent resin. Further, the bottom portion 61a of the holder main body 61 is formed with a concave portion 61j for positioning the culture vessel 23. In FIG. 12, the concave portions 61j in a circular shape inserted with bottom portions of the dishes 23C are formed at two portions.

Further, a shape and a size of the concave portion 61j formed at the bottom portion 61a of the holder main body 61 are determined in accordance with the kind and the size of the culture vessel 23 held by the holder main body 61. For example, when the well plate 23A or the flask 23B is used as the culture vessel 23, the concave portion 61j is formed in accordance with the shape and the size of the bottom portion of the well plate 23A or the flask 23B, and positioning is carried out by inserting the bottom portion of the well plate 23A or the flask 23B to the concave portion 61j.

Further, according to the embodiment, an outer shape of the holder main body 61 is constituted by the same shape for a plurality of kinds of the culture vessels 23 mounted on the holder main body 61 and having different outer shapes, for example, three kinds of the culture vessels 23 of the well plate 23A, the flask 23B, the dish 23C. The same shape of the outer shape signifies that at least a height H, a length L and a width W of the holder main body 61 stay the same.

According to the holder for the culture vessel of the embodiment, the holder main body 61 held and transferred by the transfer device 15 is formed with the concave portions 61f, 61h for positioning the holder main body 61 on the sample base 41 of the observation stage 38, and therefore, the holder 21 can easily and firmly be positioned to the predetermined position of the sample base 41 of the observation stage 38.

Further, the holder main body 61 is formed with the concave portion 61j for determining a position of the culture vessel 23 mounted on the holder main body 61, and therefore, by changing the shape and the size of the concave portion 61j, the culture vessel 23 can easily and firmly be transferred by the same transfer device 15 regardless of the kind of and the size.

Further, according to the embodiment, by constituting a wall thickness t4 from the bottom face of the concave portion 61j of the holder main body 61 to the bottom face of the holder main body 61 by a wall thickness which differs in accordance with the wall thickness (for example, t1, t2, t3 of FIG. 6) of the bottom face of the culture vessel 23 mounted on the holder main body 61, regardless of the kind of the culture vessel 23, the optical length from the object lens of the microscope 42 to the sample in the culture vessel 23 can be made to stay the same. Further, in this case, the wall thickness adjusting sheet 63 shown in FIG. 7 can be dispensed with and a reduction in cost can be achieved.

Fourth Embodiment

Figure 14:
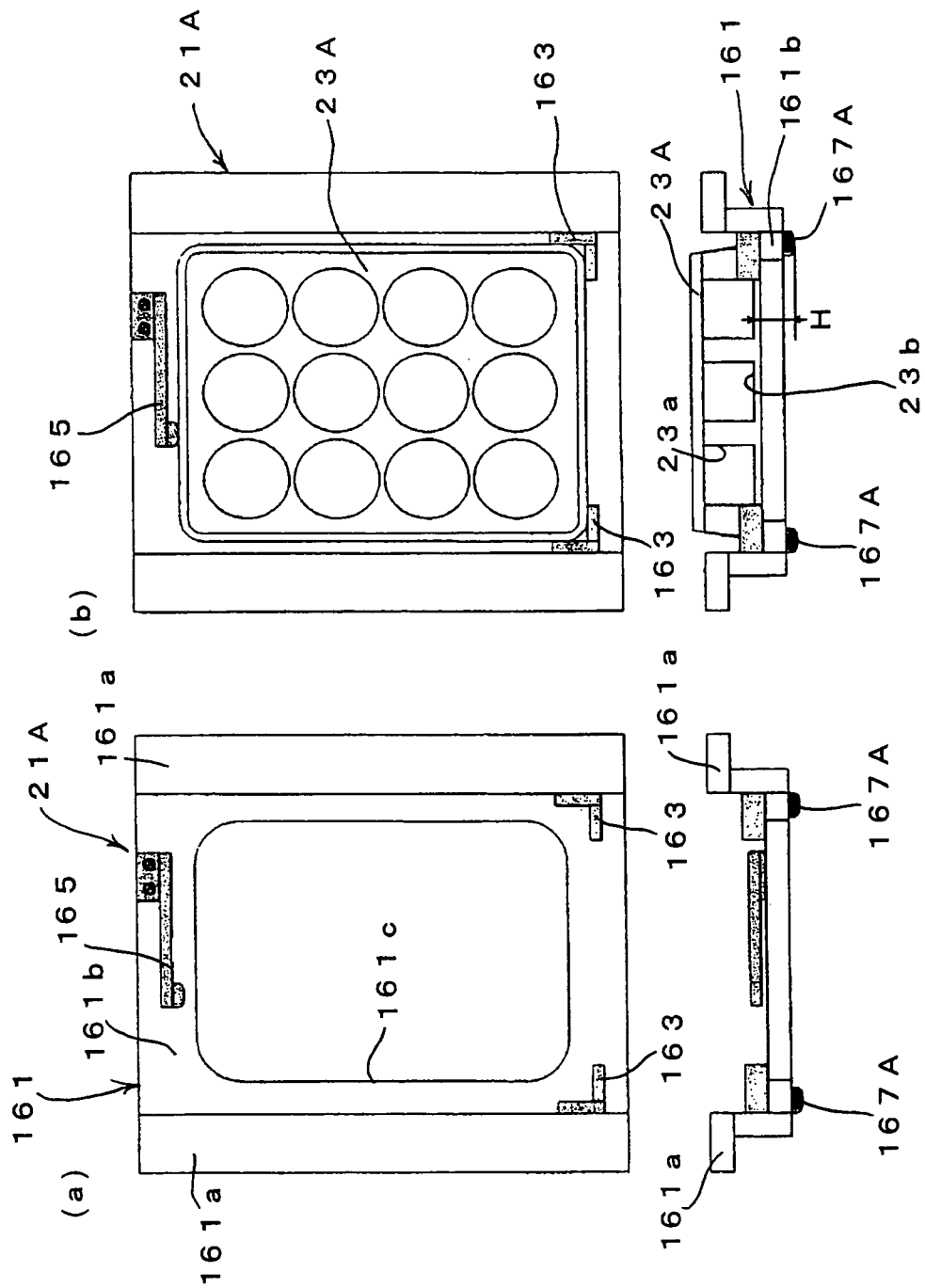
FIG. 14 illustrates explanatory views showing a well plate held by a holder.

FIG. 14 shows other embodiment of the holder for the culture vessel of the invention. Further, in the embodiment, members the same as those of the second embodiment are attached with the same notations and a detailed explanation thereof will be omitted.

FIG. 14(a) shows a holder 21A for holding the well plate 23A. The holder 21A includes a holder main body 161. Both sides of an upper end of the holder main body 161 are formed with locking portions 161a for locking the transfer arm 33. A bottom portion 161b of the holder main body 161 is formed with an opening portion 161c. Further, an upper face of the bottom portion 161b of the holder main body 161 is fixed with a positioning member 163 and a spring member 165 for holding the well plate 23A. Further, a lower face of the bottom portion 161b is fixed with a leg portion 167A.

According to the holder 21A, as shown by FIG. 14(b), the well plate 23A is mounted on the bottom portion 161b of the holder main body 161 and is held at the holder main body 161 by the positioning member 163 and the spring member 165. A length of the leg portion 167A is constituted such that a height of an inner bottom face 23b of a well 23a of the well plate 23A is defined by a position of a height H from a lower end of the leg portion 167A.

Figure 15:
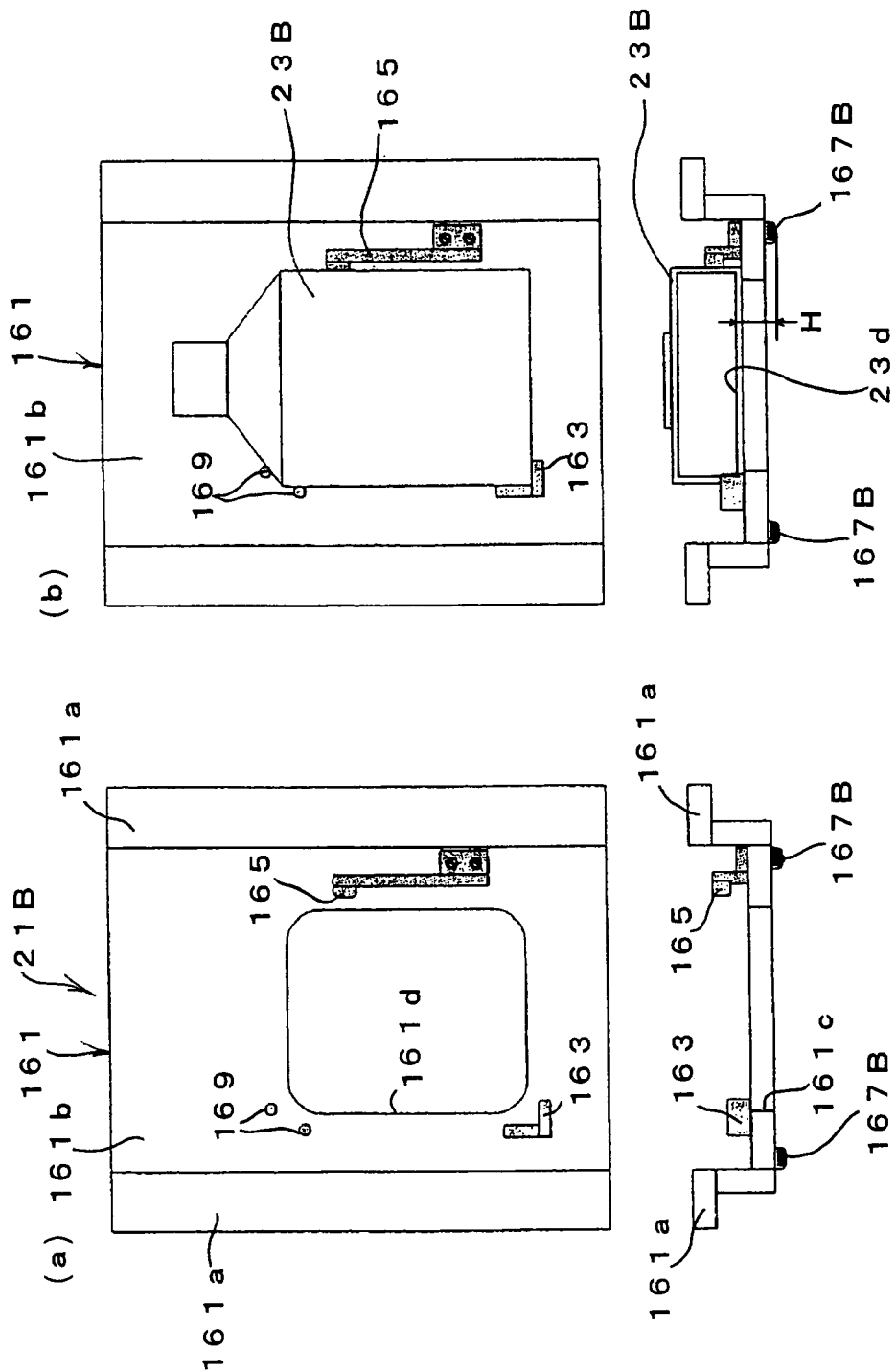
FIG. 15 illustrates explanatory views showing a flask held by a holder.

FIG. 15(a) shows a holder 23B for holding the flask 23B. The holder 21B includes the holder main body 161. The holder main body 161 is provided with an outer shape and a size the same as those of the holder main body 161 shown in FIG. 14. Both sides of an upper end of the holder main body 161 are formed with the locking portions 161a for locking the transfer arm 33. The bottom portion 161b of the holder main body 161 is formed with an opening portion 161d. Further, the upper face of the bottom portion 161b of the holder main body 161 is fixed with the positioning member 163, a pin member 169 and the spring member 165 for holding the flask 23B. Further, a lower face of the bottom portion 161b is fixed with a leg portion 167B.

According to the holder 23B, as shown by FIG. 15(b), the flask 23B is mounted on the bottom portion 161b of the holder main body 161 and is held at the holder main body 161 by the positioning member 163, the pin member 169 and the spring member 165. Further, a length of the leg portion 167B is constituted such that a height of an inner bottom face 23d of the flask 23B is defined by a position of a height H from a lower end of the leg portion 167B.

FIG. 16(a) shows a holder 21C for holding the dish 23C. The holder 21C includes the holder main body 161. The holder main body 161 is provided with the outer shape and the size the same as those of the holder main body 161 shown in FIG. 14. The both sides of the upper end of the holder main body 161 are formed with the locking portions 161a for locking the transfer arm 33. The bottom portion 161b of the holder main body 161 is formed with an opening portion 161e. Further, the upper face of the bottom portion 161b of the holder main body 161 is fixed with a pin member 171 and a spring member 173 for holding the dish 23C. Further, the lower face of the bottom portion 161b is fixed with a leg portion 167C.

According to the holder 21C, as shown by FIG. 16(b), the dish 23C is mounted on the bottom portion 161b of the holder main body 161 and is held at the holder main body 161 by the pin member 171 and the spring member 173. Further, a length of the leg portion 167C is constituted such that a height of an inner bottom face 23e of the dish 23C is defined by a position of a height H from a lower end of the leg portion 167C.

Figure 16:
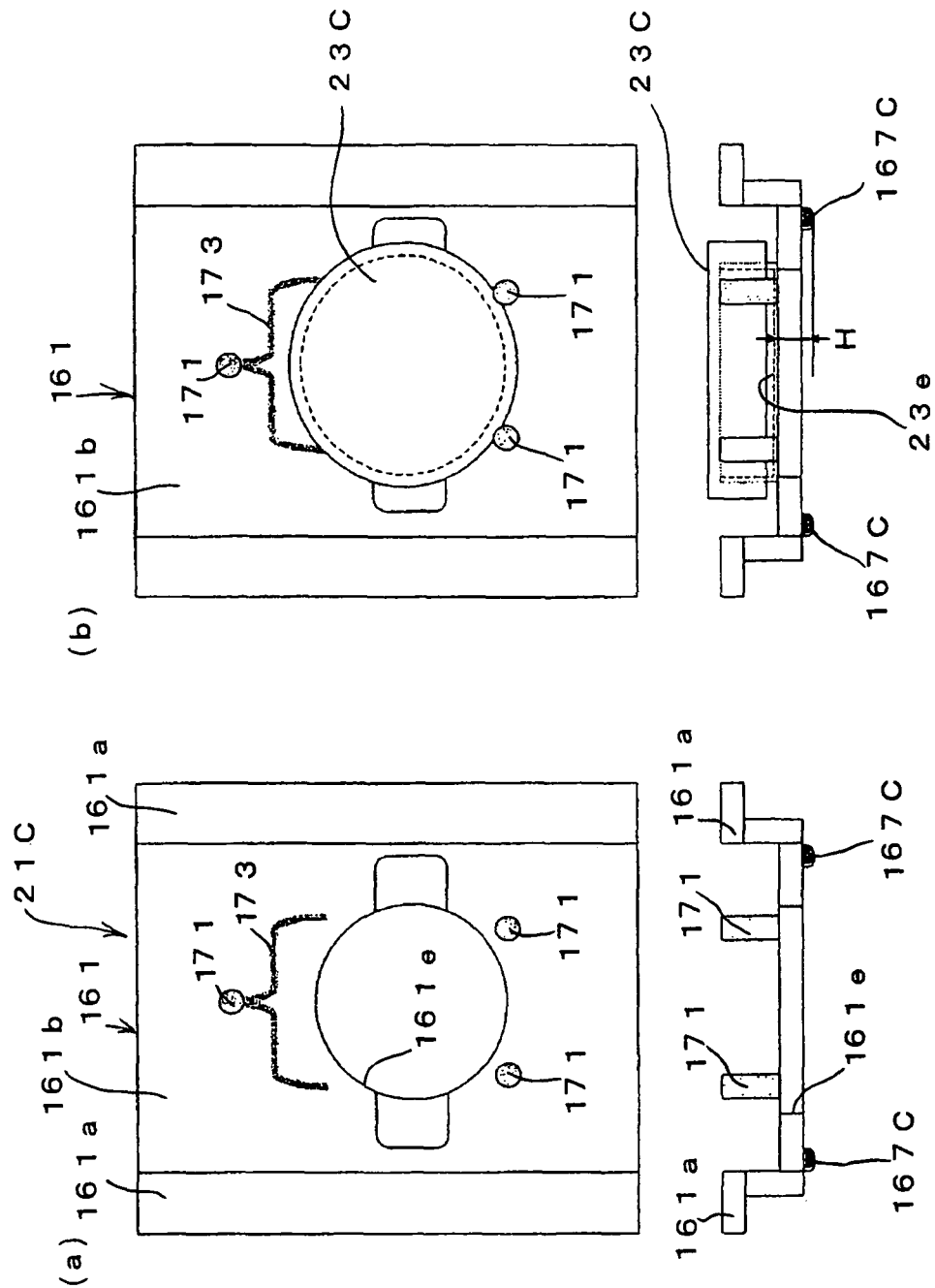
FIG. 16 illustrates explanatory views showing a dish held by a holder.
Figure 17:
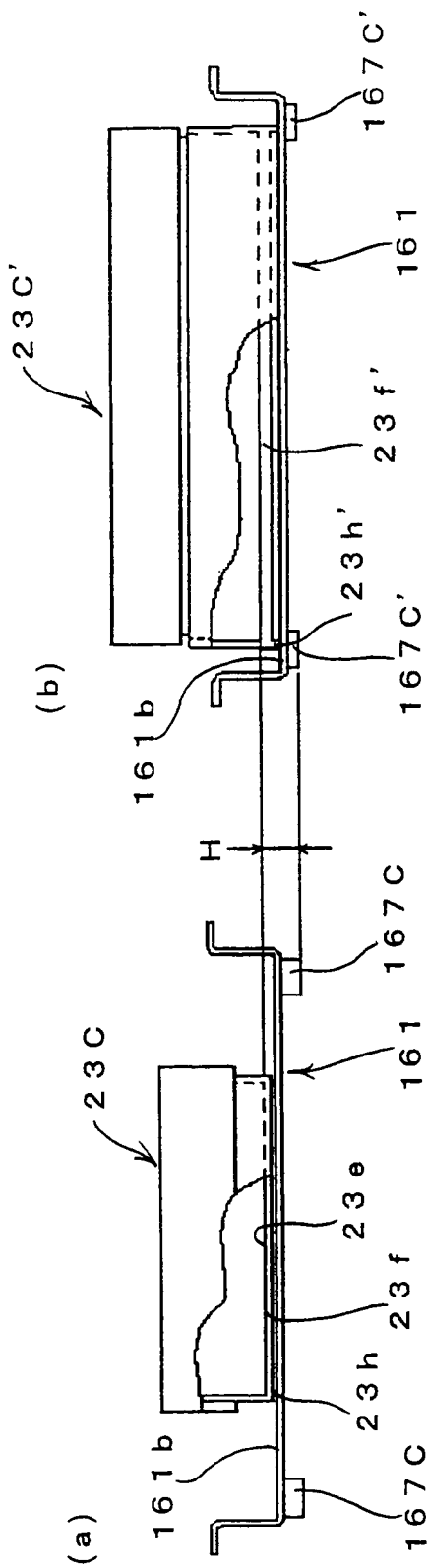
FIG. 17 illustrates explanatory views showing a length of a leg portion when dishes having different sizes are held by a holder.

FIG. 17 compares to show lengths of the leg portions 167C, 167C', when dishes 23C, 23C' having different sizes are held by the holder main body 161 shown in FIG. 16. In FIG. 17(a), the length of the leg portion 167C is set such that a value added with a wall thickness of a bottom portion 23f of the dish 23C, a height of a seat portion 23h of the dish 23C, a wall thickness of the bottom portion 161b of the holder main body 161 and a length of the leg portion 167C becomes a predetermined height H. In FIG. 17(b), a length of the leg portion 167C' is set such that a value added with a wall thickness of a bottom portion 23f' of the dish 23C', a height of a seat portion 23h' of the dish 23C', the wall thickness of the bottom portion 161b of the holder main body 161 and a length of the leg portion 167C' becomes the predetermined height H.

Figure 18:
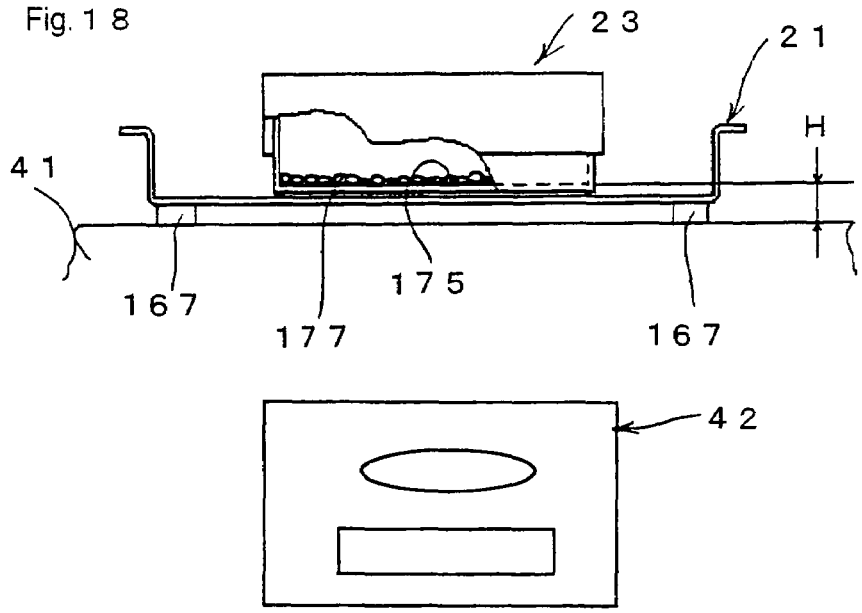
FIG. 18 is an explanatory view showing a state of observing a culture vessel mounted to a holder by an observation device.

According to the above-described holders 21 (21A, 21B, 21C), as shown by FIG. 18, the leg portions 167 (167A, 167B, 167C, 167C') are mounted on the sample base 41. Further, observation of cells 177 adhered to inner bottom faces 175 (23b, 23d, 23e) of the culture vessels 23 (23A, 23B, 23C, 23C') is carried out by the microscope 42. However, when the holders 21 (21A, 21B, 21C) are mounted on the sample base 41, regardless of the kinds and the sizes of the culture vessels 23 (23A, 23B, 23C, 23C'), the height H from the sample base 41 to the inner bottom faces 175 (23b, 23d, 23e) of the culture vessels 23 (23A, 23B, 23C, 23C') stay the same. Therefore, once adjustment of the focal point of the microscope 42 is carried out, the cells 177 adhered to the inner bottom faces 175 (23b, 23d, 23e) of the culture vessels 23 (23A, 23B, 23C, 23C') can be observed without adjusting the focal point for the respective culture vessels 23 (23A, 23B, 23C, 23C') having different kinds and sizes.

Supplementary Item Of Embodiment

Although an explanation has been given of the invention by the above-described embodiments as mentioned above, the technical range of the invention is not limited to the above-described embodiments but may be constituted by, for example, the following modes.

(1) Although according to the above-described first embodiment, an explanation has been given of an example of arranging the embodiment of the transfer device for the culture vessel of the invention at inside of the culture device, for example, the invention may be applied to a transfer device for automatically transferring a culture vessel at inside of a culture device to a precision microscope, a clean bench or the like at outside.

(2) Although according to the above-descried first embodiment, an explanation has been given of an example of manually inputting culture data to the information input portion 53, the culture data may automatically be inputted thereto by pasting an IC chip to, for example, the holder 21, the culture vessel 23 or the like.

(3) Although according to the above-described second and third embodiments, an explanation has been given of an example of forming the holder main body 61 by the white transparent resin, the holder main body 61 may be formed by, for example, a metal of aluminum or the like.

(4) Although according to the above-described second and third embodiments, an explanation has been given of an example of providing the sample base 41 on the upper side of the microscope 42 and observing cells from the lower side, the sample base may be provided on the lower side of the microscope and the cells may be observed from the upper side.

(5) Although according to the above-described second and third embodiments, an explanation has been given of an example of positioning the culture vessel 23 by the hole portion 65c formed at the template 65, or the concave portion 61j formed at the holder main body 61, the culture vessel 23 may be positioned by printing a positioning mark at, for example, the template 65 or the holder main body 61. Further, the culture vessel 23 may be positioned by forming a plurality of projections at the template 65 or the holder main body 61.

(6) Although according to the above-described fourth embodiment, an explanation has been given of an example of setting the height positions of the inner bottom faces 175 (23b, 23d, 23e) of the culture vessels 23 (23A, 23B, 23C, 23C') mounted on the holder main body 161 by the leg portions 167 (167A, 167B, 167C, 167C') fixed to the bottom portion 161b of the holder main body 161, the height position of the inner bottom face of the culture vessel may be set by interposing a height adjusting member between, for example, the bottom face of the culture vessel and the bottom face of the holder main body.

(7) Although according to the above-described fourth embodiment, an explanation has been given of an example of providing the sample base 41 on the upper side of the microscope 42 and observing the cells 177 from the lower side, the sample base may be provided on the lower side of the microscope and the cells may be observed from the upper side.

Figure 19:
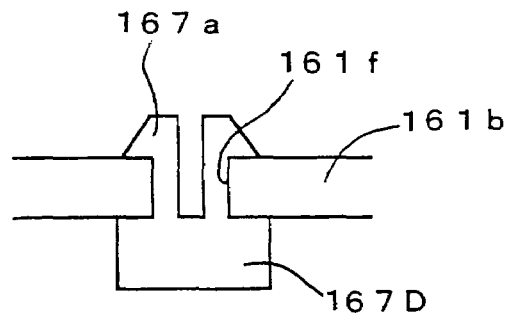
FIG. 19 is an explanatory view showing other example of a leg portion arranged at a holder main body.

(8) Although according to the above-described fourth embodiment, an explanation has been given of the example of fixedly attaching the leg portions 167 (67A, 67B, 67C, 67C') to the bottom portion 161b of the holder main body 161, for example, as shown by FIG. 19, a through hole 161f may be formed at the bottom portion 161b of the holder main body 161, a claw portion 167a of a leg portion 167D made of a resin may be inserted into the through hole 161f, and the leg portion 167D may attachably and detachably be fixed to the bottom portion 161b of the holder main body 161.

Figure 20:
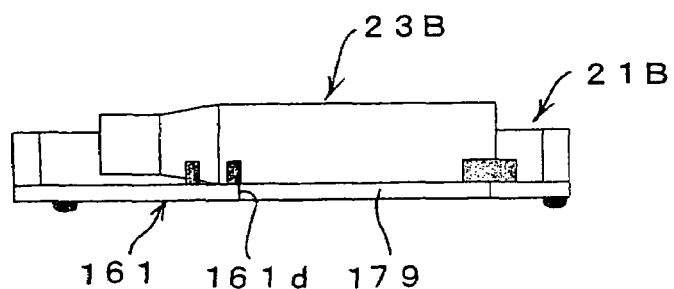
FIG. 20 is an explanatory view showing other example of a holder main body.

(9) Although according to the above-descried fourth embodiment, an explanation has been given of an example of forming the simple opening portions 161c, 161d, 161e at the holder main body 161, for example, as shown by FIG. 20, by hermetically closing the opening portion 161d of the holder main body 161 by a glass plate 179 or the like, the culture solution leaked from the culture vessel 23B can be prevented from being scattered to outside of the holder 21B.

(10) In the above-descried fourth embodiment, by constituting the holders 21 (21A, 21B, 21C) by a material of polycarbonate or the like having heat resistance, the holder can easily be autoclaved.

(11) In the above-described fourth embodiment, by pasting a bar code, an IC tag or the like to the holders 21 (21A, 21B, 21C), information of the culture vessel at inside of the holder, information of the cells at inside of the culture vessel can easily be provided.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. A transfer device for a culture vessel comprising:
   a chamber configured to maintain an atmosphere of a constant temperature and a constant humidity,
   a transferring unit provided in the chamber and configured to transfer the culture vessel for culturing a cell;
   an inputting unit configured to input information;
   a processor;
   a computer readable medium having computer instructions embodied thereon that, when executed by the processor, determines information indicating a kind of the culture vessel being input based on information input into the inputting unit indicating the kind of the culture vessel and how the kind of culture vessel differs in shape and size from other culture vessels;
   a speed setting unit connected to the inputting unit electrically and configured to set a transfer speed of the culture vessel based on the determination of the information indicating the kind of the culture vessel being input; and
   a speed controlling unit configured to control the transferring unit to allow the culture vessel to be transferred at the transfer speed set by the speed setting unit.

2. The transfer device for the culture vessel according to claim 1, wherein the kind of the culture vessel is one of a well plate, a flask and a dish.

3. The transfer device for the culture vessel according to claim 1, wherein the speed setting unit sets the transfer speed based on a past historical data with respect to the kind of the culture vessel.

4. The transfer device for the culture vessel according to claim 1, wherein
   the speed setting unit sets a transfer speed which does not give stress to the cell or a transfer speed by which a culture solution does not leak from the culture vessel due to a vibration given to the culture vessel by the transferring unit during transfer of the culture vessel.

5. The transfer device for the culture vessel according to claim 1, wherein
   the speed setting unit sets a maximum speed of the transfer speed at which the transferring unit transfers the culture vessel, and
   the speed controlling unit controls the transfer speed of the transferring unit not to exceed the maximum speed.

6. The transfer device for the culture vessel according to claim 1, wherein
   the speed setting unit sets a maximum speed of the transfer speed at which the transferring unit transfers the culture vessel so to not give stress to the cell or not to leak a culture solution from the culture vessel due to a vibration given to the culture vessel by the transferring unit during transfer of the culture vessel, and
   the speed controlling unit controls the transfer speed of the transferring unit not to exceed the maximum speed.

* * * * *